United States Patent
Bonutti et al.

(10) Patent No.: US 9,757,585 B2
(45) Date of Patent: Sep. 12, 2017

(54) MAGNETIC JOINT IMPLANT

(75) Inventors: Peter M. Bonutti, Effingham, IL (US); Justin E. Beyers, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 826 days.

(21) Appl. No.: 12/134,083

(22) Filed: Jun. 5, 2008

(65) Prior Publication Data

US 2008/0306324 A1    Dec. 11, 2008

Related U.S. Application Data

(60) Provisional application No. 60/941,957, filed on Jun. 5, 2007, provisional application No. 60/951,969, filed on Jul. 26, 2007.

(51) Int. Cl.
*A61F 2/38* (2006.01)
*A61N 2/02* (2006.01)

(52) U.S. Cl.
CPC . *A61N 2/02* (2013.01); *A61F 2/38* (2013.01)

(58) Field of Classification Search
CPC ........ A61F 2/3836; A61F 2/3886; A61F 2/38; A61F 2002/30079; A61N 2/12; A61N 2/002
USPC ............ 606/90; 600/9, 12; 623/18.12, 18.11
See application file for complete search history.

(56) References Cited

U.S. PATENT DOCUMENTS

| | | | | |
|---|---|---|---|---|
| 2,566,221 A | * | 8/1951 | Lovell .................... | G01C 19/24 310/166 |
| 3,243,238 A | * | 3/1966 | Lyman ................ | F16C 32/0408 310/90.5 |
| 3,508,444 A | * | 4/1970 | Leis .................... | F16C 32/0448 310/90.5 |
| 3,791,704 A | * | 2/1974 | Perper ................. | F16C 32/0476 310/90.5 |
| 3,815,963 A | * | 6/1974 | Wilk ....................... | H05B 6/32 310/90.5 |
| 4,024,588 A | | 5/1977 | Janssen et al. | |
| 4,057,369 A | * | 11/1977 | Isenberg ............... | F04D 19/048 310/90.5 |
| 4,271,848 A | * | 6/1981 | Turner .................... | A61N 5/04 607/101 |
| 4,585,282 A | * | 4/1986 | Bosley ................ | F16C 32/0451 104/284 |
| 4,597,379 A | | 7/1986 | Kihn | |
| 4,621,640 A | | 11/1986 | Mulhollan | |

(Continued)

FOREIGN PATENT DOCUMENTS

| | | | | |
|---|---|---|---|---|
| WO | 0027318 | 5/2000 | | |
| WO | WO 00/27318 A1 | * | 5/2000 | ............... A61F 2/64 |
| WO | WO 0027318 A1 | * | 5/2000 | |

*Primary Examiner* — Zade Coley

(57) ABSTRACT

The application is directed to devices and methods where one or more magnetic or magnetizable implants provides therapeutic benefits to a patient. The implant may be useful for expanding the range of motion of joints or dynamically providing different responses to changing conditions in the body where the implant is placed. An electromagnet is placed on or in a bone on one side of a joint, and another electromagnet or magnetically active material is placed on or in a bone on the opposing side of the joint. The electromagnet may be continuously energized to relieve pressure in the joint space, or may be energized in response to forces applied to the joint.

16 Claims, 10 Drawing Sheets

(56) References Cited

U.S. PATENT DOCUMENTS

| | | | | |
|---|---|---|---|---|
| 4,688,998 | A | * | 8/1987 | Olsen ................. A61M 1/101 415/900 |
| 4,761,579 | A | * | 8/1988 | Delassus ............. H02N 15/00 219/648 |
| 4,899,744 | A | | 2/1990 | Fujitsuka |
| 4,910,633 | A | * | 3/1990 | Quinn ................. H02N 15/00 310/90.5 |
| 4,957,498 | A | | 9/1990 | Caspari |
| 5,003,235 | A | * | 3/1991 | Groom ............... F16C 32/0465 310/90.5 |
| 5,258,007 | A | | 11/1993 | Spetzler |
| 5,281,235 | A | | 1/1994 | Haber |
| 5,332,987 | A | * | 7/1994 | Hennessy ............ H02N 15/00 310/90.5 |
| 5,334,965 | A | * | 8/1994 | Dolgin ................ B64G 1/22 335/216 |
| 5,417,701 | A | | 5/1995 | Holmes |
| 5,496,335 | A | | 3/1996 | Thomason |
| 5,556,402 | A | | 9/1996 | Xu |
| 5,595,563 | A | * | 1/1997 | Moisdon ............ A61B 17/8866 128/899 |
| 5,631,617 | A | * | 5/1997 | Morishita ............ B60L 13/10 104/285 |
| 5,649,955 | A | | 7/1997 | Hashimoto |
| 5,776,151 | A | | 7/1998 | Chan |
| 5,899,911 | A | | 5/1999 | Carter |
| 5,925,064 | A | | 7/1999 | Meyers |
| 5,947,982 | A | | 9/1999 | Duran |
| 5,955,963 | A | | 9/1999 | Wong |
| 6,099,550 | A | | 8/2000 | Yoon |
| 6,127,757 | A | * | 10/2000 | Swinbanks ............ B63G 9/00 104/293 |
| 6,154,353 | A | * | 11/2000 | Bowers ............. F16C 32/0459 361/143 |
| 6,159,224 | A | | 12/2000 | Yoon |
| 6,210,317 | B1 | | 4/2001 | Bonlie |
| 6,231,592 | B1 | | 5/2001 | Bonutti |
| 6,238,395 | B1 | | 5/2001 | Bonutti |
| 6,287,325 | B1 | | 9/2001 | Bonutti |
| 6,340,365 | B2 | | 1/2002 | Dittrich |
| 6,373,676 | B1 | * | 4/2002 | Baker ................. H02N 15/00 361/143 |
| 6,387,096 | B1 | * | 5/2002 | Hyde, Jr. ............. A61N 2/06 606/60 |
| 6,776,753 | B1 | | 8/2004 | Holcomb |
| 6,779,871 | B1 | | 8/2004 | Seto et al. |
| 6,796,973 | B1 | | 9/2004 | Contente et al. |
| 6,849,076 | B2 | | 2/2005 | Blunn et al. |
| 6,911,754 | B2 | * | 6/2005 | Johnson ............... F16F 15/03 310/51 |
| 6,955,172 | B2 | * | 10/2005 | Nelson ................ A61F 5/566 128/848 |
| 7,029,432 | B2 | | 4/2006 | Woo |
| 7,101,374 | B2 | * | 9/2006 | Hyde, Jr. ............. A61N 2/06 606/60 |
| 7,110,236 | B2 | * | 9/2006 | Joachim ............. H02N 15/00 361/139 |
| 7,195,645 | B2 | * | 3/2007 | Disilvestro ........... A61B 5/076 600/587 |
| 2001/0029400 | A1 | * | 10/2001 | Deffenbaugh ......... F16F 9/535 623/24 |
| 2002/0032484 | A1 | * | 3/2002 | Hyde, Jr. ............. A61B 17/68 623/18.12 |
| 2002/0066450 | A1 | * | 6/2002 | Bonutti ............ A61M 16/0488 128/200.26 |
| 2002/0103495 | A1 | | 8/2002 | Cole |
| 2003/0236572 | A1 | * | 12/2003 | Bertram, III ............ A61F 2/40 623/18.12 |
| 2004/0052029 | A1 | * | 3/2004 | Joachim ............... H02N 15/00 361/143 |
| 2004/0059423 | A1 | * | 3/2004 | Barnes ................. A61B 17/58 623/18.12 |
| 2004/0193266 | A1 | * | 9/2004 | Meyer ................. A61F 2/46 623/16.11 |
| 2005/0234555 | A1 | * | 10/2005 | Sutton ................ A61F 2/442 623/17.15 |
| 2005/0251080 | A1 | * | 11/2005 | Hyde ................. A61F 2/3836 602/26 |
| 2005/0256571 | A1 | * | 11/2005 | Azar ................. A61F 2/1613 623/6.22 |
| 2006/0036323 | A1 | * | 2/2006 | Carl ................... A61F 2/4405 623/17.11 |
| 2006/0047283 | A1 | * | 3/2006 | Evans, III ............ A61B 5/1076 606/102 |
| 2006/0058790 | A1 | * | 3/2006 | Carl ................... A61B 17/70 606/248 |
| 2006/0149277 | A1 | * | 7/2006 | Cinquin ............. A61B 17/025 606/90 |
| 2006/0149338 | A1 | * | 7/2006 | Flaherty ............. A61H 1/0255 607/49 |
| 2006/0247782 | A1 | * | 11/2006 | Molz, IV ............. A61F 2/442 623/17.16 |
| 2007/0050030 | A1 | * | 3/2007 | Kim .................. A61B 17/7059 623/17.11 |
| 2007/0100457 | A1 | * | 5/2007 | Hyde ................. A61B 17/88 623/18.12 |
| 2007/0179493 | A1 | * | 8/2007 | Kim .................. A61B 17/7062 606/33 |

* cited by examiner

MAGNETIC JOINT IMPLANT

CROSS-REFERENCE TO RELATED APPLICATIONS

This application claims priority of U.S. provisional patent application Ser. No's. 60/941,957 filed Jun. 5, 2007, and 60/951,969 filed Jul. 26, 2007, both of which are hereby incorporated by reference in their entirety.

FIELD OF THE INVENTION

The present invention relates to methods and devices using magnetic materials and electric or magnetic fields to provide therapeutic benefits to a patient.

BACKGROUND OF THE INVENTION

Magnetic devices and electric or magnetic fields have been used in the past for the purpose of providing medical benefits to people. Some of these medical benefits are more direct than others. In some instances, one or more magnets are simply disposed near an area to be treated based on a belief that exposure to a magnetic field would holistically cure human afflictions, ailments, and diseases. Some examples of the placement of magnets near a treated area to bring about holistic therapy include U.S. Pat. Nos. 7,029,432 to Woo, 6,796,973 to Bates, and 6,776,753 to Holcomb. Similarly, U.S. Pat. No. 6,210,317 to Bonlie describes a method of treating a patient who lives in a relatively weak magnetic field by providing a device having high intensity unidirectional magnetic field aligned to pass through the patient's body in a particular manner.

In other therapeutic applications, magnetic devices have been used to help control the position of an implant in a patient's body. U.S. Pat. No. 6,849,076 to Blunn, for example, uses magnets and electric fields to non-invasively apply extending or tensioning forces to a distraction device disposed in bone. Likewise, U.S. Pat. No. 4,024,588 to Janssen describes an artificial joint that uses magnets or magnetizable elements to attract or repel component of the joint, and U.S. Pat. No. 6,387,096 describes the use of an array of magnets to secure and align portions of treated bone.

Magnets also have been used to attract materials to a part of the body. U.S. Pat. No. 6,779,871 to Halpern, for instance describes a method for repairing cartilage by deploying a porous, magnetic scaffold at the damaged site and injecting magnetically tagged growth promoting material near the area of the defect. The magnetically tagged growth promoting material is then drawn into the apertures of the porous scaffold by magnetic attraction.

While these prior uses of magnets and electric or magnetic fields may have had varying degrees of efficacy, none of them provided the ability to dynamically adjust to changing conditions in the treated area. In addition, none of these prior devices and treatment methods provided the capability to be used in treating a joint by causing it to move through at least a portion of its range of motion or through a repeated cycle of relative motion between two elements implanted in the treated area. Furthermore, past uses of magnets in medical therapy have not been utilized to help contain a therapeutic agent to a treated area.

SUMMARY OF THE INVENTION

The invention relates to the use of magnets and electric or magnetic field in the treatment of a joint, bone, or other tissue. More specifically, one embodiment of the invention relates to the use of magnets and electric or magnetic fields to perform arthrodiastasis in a patient. One example of this embodiment may involve a method of implanting first and second elements into portions of the patient's bone or joint. One or both of the elements may be selectively magnetized so that they are either attracted toward each other or repelled further apart by the magnetic fields associated with the components.

Another embodiment of the invention may involve a method of maintaining first and second bone portions within an acceptable or desired range of positions or distances from each other. First, magnetic or magnetizable elements are deployed in the treated area. Then, as conditions near the first and second bone portions change, such as when the patient increases or reduces loading on the treated area, the magnetic field of one or more elements may be varied in response to changes in loading, body position, or other factors. In this manner, the space between the first and second bones may be better maintained within an acceptable range, at a desired distance, or within more acceptable loading conditions.

Some variations of this embodiment of the invention may relate to ways to provide dynamic control of the magnetic field in the treated area. For example, one or more magnetic fields may be adjusted by altering the voltage supplied to it. More specifically, the applied voltage to one of the electromagnets may decrease with a decrease in pressure exerted in the treated area, on a bone, or at a joint. Likewise, increases in pressure in the treated area, bone or joint may result in increased voltage being supplied to one or more electromagnets.

In some embodiments, a baseline voltage applied to one or more electromagnets may be monitored for variations. These variations may indicate changing conditions are occurring in the treated area that warrants a change in an applied voltage. One example of how a baseline and applied voltage could be used is by utilizing a square wave to power one or more electromagnets.

Another embodiment of the invention utilizes magnets and electric or magnetic fields to help retain pharmaceutical materials at a desired location in the body. For example, a magnet or magnetizable material may be placed in a bone that is to be treated with Bone Morphogenetic Proteins (BMPs), which are a group of growth factors known for their ability to induce the formation of bone and cartilage. BMPs are useful for triggering bone growth where it is deployed, but it may be desirable to contain it to a treated area where bone growth is desired. To help contain BMP to an area where bone growth is desired, the BMP may be associated with magnetic particles so that when it is placed in the treated bone the magnetic attraction helps reduce the likelihood of BMP leaking into areas outside of the treated bone.

Herein, magnetically active refers to magnets, electromagnets, or materials significantly attracted or repelled by same due to being magnetically permeable, and a magnetically active implant refers to an implant comprised of or containing a magnetically active material. Magnetic materials include neodymium, samarium-cobalt, ceramic, alnico, injection molded/bonded, and plastic magnets, made from organic polymers. Polymer magnets may include biocompatible and biodegradable polymers. Representative examples of magnetically permeable materials include, but are not limited to, mumetal, permalloy, iron, steel and soft ferrite.

Various joint pathologies may be addressed by compressing or distracting the joint, or by compressing or distracting one side of a joint, medially or laterally, or by compressing one side of a joint while distracting the other side. It may further be beneficial to change these therapies during the course of healing. Thus, in another embodiment of the invention, a magnetically active implant is placed on one or both sides of a joint. It should be understood that if two implants are intended to attract each other, at least one of the two must be magnetized or magnetizable material, and the other may merely be magnetically permeable, so that attraction may be achieved.

The implants are configured and arranged so that any of the various permutations of attraction or repulsion are accomplished. For example, the medial and lateral portions of a joint may be compressed, wherein the medial and lateral portions of both sides of a joint are attracted to each other, or distracted, wherein the medial and lateral portions of both sides of a joint are repelled from each other. Alternatively, the medial and lateral sides of a joint may undergo different forces, whereby if the medial sides are attracted, the lateral sides are repelled, and if the medial sides are repelled, the lateral sides are attracted.

The implant may be an elongated form, such as a pin or screw having a uniform magnetic field throughout its length. Alternatively, there may be more than one magnetic field, with like or reverse flowing magnetic fields. These fields interact on each side of the joint, producing compression or distraction as described above.

Alternatively, the implant is advantageously sized and shaped to fit the anatomy of the joint, to advantageously occupy a particular space available in the area of the joint, such as on the surface of a bone, either on the load bearing portion of the joint, or proximate the load bearing portion of the joint, or within the interior of the bone, or within a relief or channel formed in the bone, proximate the joint.

It is convenient, in a further embodiment of the invention, for an implant including a magnetically active material to be formed in a variety of shaped forms, such as spheres, elliptical spheres, cones, cuboids, rods or combinations thereof, in a range of sizes. In this manner, the surgeon may select from a tray or kit containing an assortment of such implants, and may arrange implants of like or dissimilar sizes within the joint, in order to achieve the desired results, such as field strength and direction, while conforming to the anatomical space available.

The implants may be provided with a porous surface, or may have apertures, to promote bone ingrowth. The implants may further be coated with material which promotes bone growth and or ingrowth.

In yet another aspect of the invention, movement of a joint is influenced by an external device. In this embodiment, magnetically active material is implanted in engagement with at least one bone associated with a joint. An external device contains magnetically active material, which is attracted to the implanted material. In this manner, braces, internal or external fixators, therapy devices and the like may interact with the limb with reduced or eliminated contact with the skin, and without the need for skin penetrations.

For example, a brace is fastened to a limb on one side of a joint, and magnetically promotes, controls, or arrests movement of the joint through magnetic interaction between the brace and the implants located on the other side of the joint. Further, both sides of the joint may interact with the brace magnetically, whereby the brace does not contact the skin at all. The brace and or implants may be provided with a power source, whereby the magnetic fields and thus the behavior of the brace are controllable through electronic or other means.

Implants in accordance with the invention may also be used in association with soft tissue; increasing, maintaining, or decreasing the amount of space defined by the soft tissue. Implants are fastened to soft tissue, and through magnetic interaction with other implants in proximity, are attracted or repelled in connection with the soft tissue, thus modifying the location or the shape of the space defined by the soft tissue. Magnetically active implants attached to soft tissue are arranged to attract and or repel each other in order to increase or decrease the volumetric space, to block or allow the passage of fluids or other materials within a vessel or chamber, or to maintain separate soft tissue together, or apart. The implants comprising magnetically active material are attached by mechanical means, including bands, adhesives, sutures, staples, and clips, or by magnetic attraction, as by pinching soft tissue between two magnetically active members.

Soft tissue which has been abraded, cut, or damaged, as by surgery or trauma, may be separated from other tissue through the use of magnetically active implants as described above, and thus maintained in non-contacting conformity while healing, thereby reducing the incidence and severity of the formation of adhesions.

It is further contemplated that one or more magnetically active elements are located outside the body, operative to attract a magnetically active implant associated with soft tissue, and thus influence the location, shape or position of soft tissue within the body.

In yet another embodiment in accordance with the invention, soft tissue is positioned or shaped with respect to bone, or is connected to bone, using at least one magnetically active implant.

In another embodiment of the invention, magnetic shielding is provided to control the force of magnetic fields between magnetically active implants. Shielding is accomplished using known methods, such as placing a magnetically permeable material between a magnetically active implant and another magnetically active implant, or between a magnetically active implant and a magnetically active material which is not intended to be influenced by the magnetically active implant. The shielding may be selectively positioned to be interposed between two or more magnetically active members where it is intended to disrupt the magnetic field, and removed or repositioned when it is desired to restore the magnetic field.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
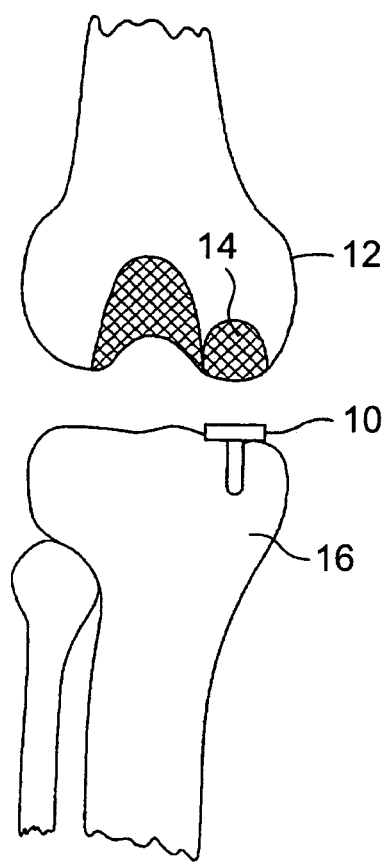
FIG. 1 is an illustration of one embodiment of the invention implanted in a knee joint.

As mentioned above, the invention relates to new methods and devices for treating a patient through the use of magnets and electric or magnetic fields.

One application of the invention may be to facilitate a treatment known as arthrodiastasis, which can be used as a treatment program for arthritis. For instance, a mechanical device may be placed in a treated area of the patient to internally distract a joint. One example of this aspect of the invention may be an intramedullary rod linked to a plate or to another rod. One or both of the elements of the mechanical device may be made of magnetic material, an electromagnet, or a magnetizable material. Preferably, both elements are capable of responding to magnetic forces. Thus, changes in intensity and/or polarity of one or more magnetic fields associated with one or more elements causes two or more elements to undergo greater or lower amounts of forces of repulsion or attraction.

Once the device is placed in the patient's body, in this case a knee is illustrated, the magnetic field of at least one element may be varied so that the elements are able to be progressively distracted or attracted to each other. The variation of the magnetic field may be accomplished by providing an electronically adjustable component that is capable of changing the intensity and/or polarity of the magnetic field of at least one element of the device. The device may be cycled through a range of positions or conditions that help restore or maintain range of motion of the joint.

The ability to vary the intensity and/or polarity of the magnetic field of one or more elements may be used to cause the treated area to move through a range of motion or to cycle through two or more positions. This movement could be accomplished with or without assistance from the patient. For instance, in one embodiment the patient may undergo a therapeutic regimen where they are asked to exercise the treated area by actively moving it through a range of motion either freely or under a resistive load. In other words, movement of the treated area relies at least in part upon the patient exerting energy to bring about the motion.

There may be instances where one or more electromagnets assist the patient in moving the treated area. For example, a patient recovering from an injury or surgical procedure may initially be unable to move the joint or treated area, or alternatively may have limited movement. A dynamically controlled electromagnetic implant may be used to assist the movement of the joint or treated area. As the patient's recovery progresses, the frequency and degree of assistance may be reduced. Thus, this embodiment of the invention may help restore motion to a joint or treated area by providing targeted assistance to the patient.

As indicated above, the ability to assist a patient in movement may be used in therapeutic sessions with the patient, but the implant also may be used to assist the patient at other times. For example, the implant may be able to help the patient change from one position, such as sitting in a chair, to another position, such as standing.

In addition to the above, another possible use of this embodiment of the invention is to cause relative motion of the implant elements without exertion or assistance from the patient. For instance, if a patient is unable to move the treated area, bone or joint in a desired manner or direction, the electromagnets of the implant may be used to provide that motion. The direction of motion may be similar to at least a part of the normal range or motion the treated area or joint may undergo. For example, magnetic fields of an implant in a knee joint may be controlled to cause the joint to bend.

Alternatively, or in addition to potentially causing the treated area, bone or joint to at least partially move through its normal direction, varying the electromagnetic forces of the implant may be used to move the treated area or joint in a different manner. For instance, the elements of the implant may undergo varying magnetic intensity and polarity so that the parts of the body the elements are associated with may alternate between states of undergoing magnetic attraction and being repelled apart.

Likewise, this embodiment of the invention may be used to bring about other types of motion instead of, or in addition to, linear movement. For instance, the implant may be used to cause rotation, bending, or any combinations of movement.

The ability to cause movement in the treated area or joint without requiring the patient's assistance may allow physicians to consider a greater variety of treatment regimes. For example, some treatments may be automated or scheduled. The ability to schedule or automate at least portions of a patient's treatment may be of particular interest if the desired movement is relatively small or minor, such as incremental movements of the elements that may allow improved blood flow, better access by therapeutic agents, reduced inflammation, or the like. It should be noted, however, that this feature may be an available consideration for more significant movement as well.

The use of magnets and magnetic or electric fields also may be used to help control forces or relative positioning between two bones, implant components, other tissues, or any combinations thereof. FIG. 1 illustrates one embodiment of the invention with this capability. In particular, FIG. 1 shows a first implant component 10 disposed in a first bone 12 and a second implant component 14 disposed in a second bone 16. For purposes of illustrating the invention, the joint in this example is a knee. It should be noted, however, that skilled artisans having the benefit of this description would appreciate that the invention could be used in other joints as well, such as a finger, wrist, elbow, shoulder, spine, hip, ankle, toe or the like.

If the joint between the two bones is damaged, the implant component may be inserted into the bones during a surgical procedure to help repair or remediate the joint. Alternatively, the implant may be inserted into position in a separate procedure.

Figure 2:
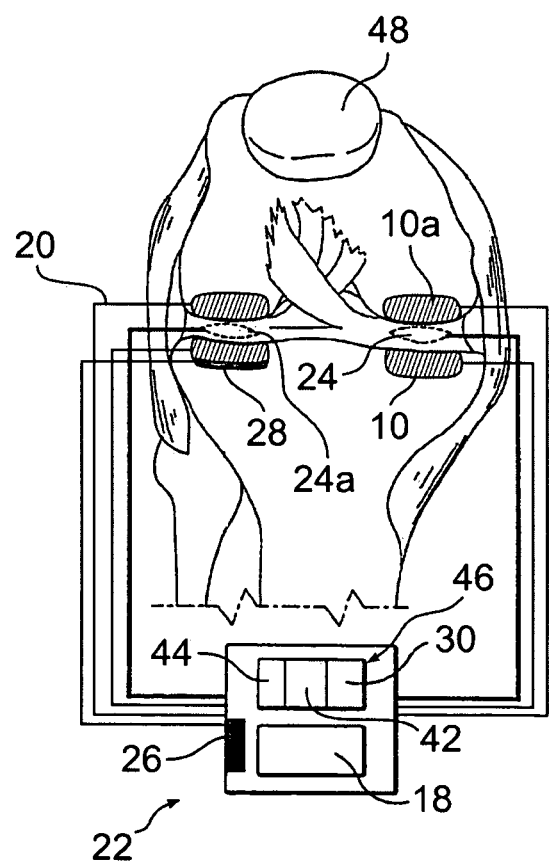
FIG. 2 is an illustration of an additional embodiment in accordance with the invention, further illustrating a dynamic control in a knee.

In the example shown in FIG. 2, both implant components 10, 10a may be electromagnetic, so that the intensity and/or polarity of the implant components may be varied depending upon conditions near the joint. Thus, the degree to which the implant components may be attracted to or repelled away from each other may vary dynamically.

For instance, dynamic control of the amount of electromagnetic force could be configured to allow the magnetic field to lower when the joint is not bearing weight. Conversely, when the patient is standing or otherwise imparting loading on the joint, the electromagnetic forces may be increased to help repel the bones from imparting unacceptably high loads on the joint. The degree of repelling force provided can be varied, tuned, or optimized to provide greater comfort to the patient.

A battery pack 18 or other power source may be associated with the implant to help vary the electromagnetic forces of the implant components. The battery pack or power source may be configured so that it may be in a housing 22 near the joint, such as in a brace that the patient may selectively place around or near the joint or removed when dynamic control of the magnetic forces is not needed or desired. If a brace is used, it also may provide additional support to the treated area, bone, or joint by either further distributing loading forces to a greater area or by helping resist joint movement in an undesired direction. As the need for greater repelling force is detected, the voltage supplied to the implant components may be increased. Adjustments to the amount of magnetic force provided by the implant preferably can be controlled dynamically so that the implant adjusts to changing loading or other parameters in the treated area, bone, or joint.

Figure 4:
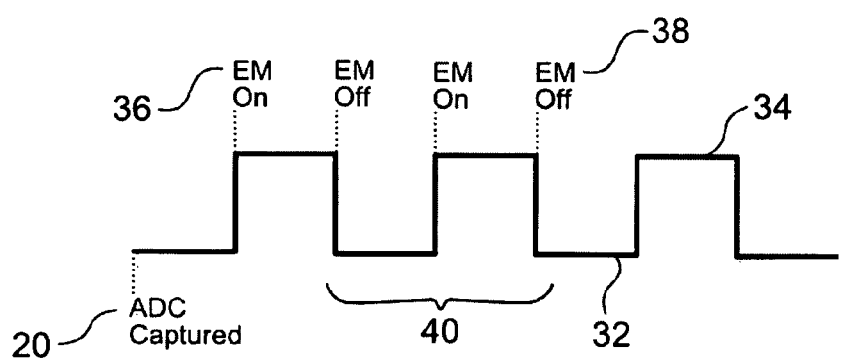
FIG. 4 is an illustration of a pulse-width modulated signal powering an electromagnet, and having a baseline voltage and an applied voltage.

There are several ways to provide dynamic control of the amount of electromagnetic force imparted by the implant components. One example may be to use a square wave to power the electromagnetic components, as shown in FIG. 4. The voltage may then be monitored and compared with known electrical properties of the device.

Additional voltages seen at the electromagnet, captured through known means 20, as during a low period 32 of the square wave, are operative to indicate that the distance between the two components has changed. In particular, when the joint is bearing weight, the implant components may move closer toward each other. This movement in response to loading may cause a change in the square wave 34. This change would result from a change in the magnetic field caused by the movement of the joint or implant components relative to each other.

Figure 3:
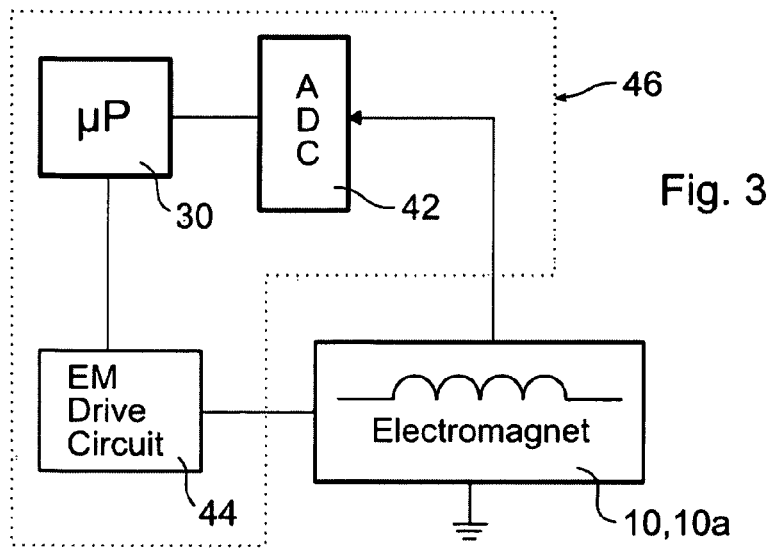
FIG. 3 is a diagrammatic illustration of a dynamic control system in accordance with the invention.

Thus, changes 40 in the square wave may be monitored and used to determine how to dynamically control the amount of electromagnetic force that is needed. In particular, one or more component of the implant may be subjected to a baseline voltage and an applied voltage. During the period of applied voltage, the intensity and/or polarity of the magnetic field of the implant element may be increased or changed. The amount of voltage applied during this state may be varied, such as, with reference to FIG. 3, by a drive circuit 44, to provide dynamic responses to changing conditions in the treated area.

The baseline voltage can be used to help detect when a dynamic response is needed. For example, movement or changed conditions in the relative position of the implant elements may cause changes in the baseline voltage. As these voltage changes are detected, for example by an analog to digital converter 42, increases 36 or decreases 38 can be made to the applied voltage. Thus, as a patient changes from a sitting position to a standing position, for example, the relative movement of the implanted elements can be detected and a response determined dynamically.

Figure 4A:
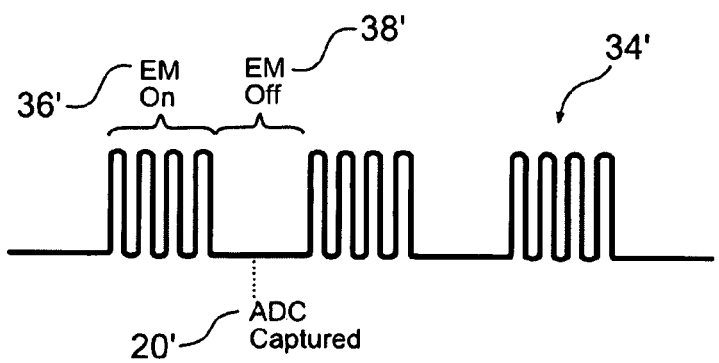
FIG. 4a is an illustration of an alternative pulse-width signal in accordance with the invention.

With reference to FIG. 4A, an alternative control method employs pulse-width modulation 34', with a period of energizing one or more implanted electromagnets illustrated during the portion of the waveform indicated as 36', with electromagnets off during the period indicated as 38'. FIG. 4 illustrates a simple form of pulse-width modulation, having a duty cycle (on-time) of 50%, in the example shown. Duty cycle, or duty factor, represents the product of the pulse duration and pulse repetition frequency of a pulse carrier, equal to the time per second that pulse power is applied. The signal can be varied, with an alternate duty cycle, as is shown in FIG. 4A, or with further variations in the wave form, as would be understood by one skilled in the art. For example, a more complex wave form may be output, wherein power to the electromagnets, or duty cycle, is modulated, to produce smooth transitions or other dynamic effect. Additionally, the voltage level may be adjusted, the duty cycle may be adjusted, or a combination of adjustments to the voltage level and duty cycle may be made, for precise control. Thus, in accordance with the invention, alternating as well as direct current energy sources may advantageously be utilized as drive voltage.

There may be other ways to detect a need for a dynamic response other than from looking at indicia of relative movement of implanted elements. One example could be that the implant element may provide different responses, signals, or characteristics depending upon the degree of pressure, shear, or other forces it may be subjected to. This capability may be carried out in a similar manner as strain gauges are able to respond to forces applied to them. As the degree of forces applied to an element intensifies, it may be beneficial to dynamically change the magnetic field of the element. Alternatively, a separate force detecting device 24 may be used.

Dynamic control of electromagnetic forces may be accomplished in other ways as well. For instance, the implant may be associated with an apparatus that monitors or detects changes in the biologic microenvironment or microclimate of a body region or treated area, such as a joint or bone, within a joint space, or within a joint capsule.

One example of such an apparatus may include a sensor 24a, as can be seen in FIG. 2, disposed in the treated area that measures one or more microenvironment parameters. Based on predetermined levels or parameters, the sensor may send a signal to a control unit 46 indicating that conditions in the treated area have changed. As the detected changes exceed a threshold, the electromagnetic forces of the implant may be altered.

Instead of, or in addition to changes in relative position of bones, implants or other tissue in the treated area or measuring pressure or other forces in the area, there may be other changes in the microenvironment that could be monitored or detected and used to provide a dynamic response. An increase in temperature of a treated area may indicate, for example, that the joint, bone, or part of the body is in use. A knee joint, for example, may exhibit an elevated temperature during states of use compared to states of rest. Similarly, temperature differences may indicate the patient is asleep or fully at rest while higher temperatures may indicate that the patient is awake. The concepts associated with using temperature to provide dynamic control may also apply to blood pressure or heart rate. If the device operates on a battery, knowing when to apply therapeutic relief or treatment to the patient may provide an additional benefit of improving power management of the system.

Other changes in the microenvironment also may be used for dynamic control. Viscosity of fluid in the treated area, for example, may also change during periods of use versus non-use. A positioning or orientation sensor may be used to detect, for example, when the patient is sitting, standing or lying down. Such a sensor may also be used to determine the orientation of the treated area instead of the patient's overall body position.

An orientation sensor 26 may be placed externally to the patient's body, such as being integrated in or removably coupled to a brace, or may be associated with the implant disposed in the patient's body 28. Still other changes in the microenvironment may be used as well, such as detecting muscle activity, or levels of different materials in blood or other body fluids. Oxygen or acid levels, for instance, may also be indicators that could be used to help dynamically control the implant.

Controlling the electromagnetic forces in the microenvironment may be performed automatically by one or more microprocessor 30 based on present parameter levels and input signals from the sensor. The electromagnetic forces may alternatively, or additionally, be manually controlled by a physician, assistant, or patient. Thus a patient feeling discomfort in the treated area may manually alter the amount of electromagnetic force exerted by the implant.

Other ways to achieve dynamic control conditions in a treated area are described in co-pending U.S. patent application Ser. No. 11/867,679, entitled "METHODS AND DEVICES FOR CONTROLLING BIOLOGIC MICROENVIRONMENTS" and filed on Oct. 4, 2007, the entirety of which is hereby incorporated by reference.

Yet another application of the invention is to help concentrate a pharmaceutical agent to a local site. By charging pharmaceutical agents, cells, gene therapy agents, RNA, DNA, BMP, tissue inductive factors, and the like, these substances may be concentrated at a treated area or microenvironment region with assistance of a magnet or magnetizable component as previously described.

In one embodiment, the charged substances may be introduced into the patient's blood stream and circulate in the body until an externally mounted or internally implanted magnet or magnetizable component draws the charged particles to a local region. The magnetic energy may also pull the charge substances from a bloodstream, through the vessel wall, and into adjacent tissue. Introduction of charge pharmaceutical agents into the blood stream may be accomplished by injection, digestion, transdermally, or by any other suitable means.

In some instances, it may be desirable to contain or restrict a pharmaceutical agent to a particular area. For instance, it may be desirable to control bone cement injected into a repaired vertebral body of the spine so that the material does not leak out of the treated area or vertebral body. Prior to injecting the pharmaceutical agent into the treated area, bone or joint, the pharmaceutical agent may be charged or associated with compounds, materials or processes that make the pharmaceutical agent responsive to magnetic forces. The treated area may then include a magnetic or magnetizable material so that the pharmaceutical agent is more likely to remain confined to a desired location.

As described above, the intensity and/or polarity of the magnetic implant may vary dynamically or over time. For example the intensity of the magnetic field of the element may initially be high, but over time as the risk of the pharmaceutical agent escaping becomes lower the amount of magnetic force needed can likewise be reduced. The implanted element also may be made of a resorbable material that over time loses its magnetic capabilities.

The implanted elements used for any of the embodiments described herein may be made of a variety of materials. For example, one or more elements may be a magnetic compound or material in a polymeric material formed into the shape of a fastener, screw or other implant element. The polymeric material can be coupled or attached to other components. Alternatively, the polymeric material could be attached or otherwise associated with a bone, joint, or other part of the body.

The materials also may be paramagnetic, which could be implanted and magnetized later or repeatedly once they are in the body. These paramagnetic materials could be laminated, could be layered, or could be put in as fibrous material. The also could be placed in somewhat flexible sheets or rolled up during implantation and unrolled once in a desired position. In addition, the paramagnetic materials, if used, may have amplified magnetic capability if combined or used with electromagnetic processes or devices.

Figure 5:
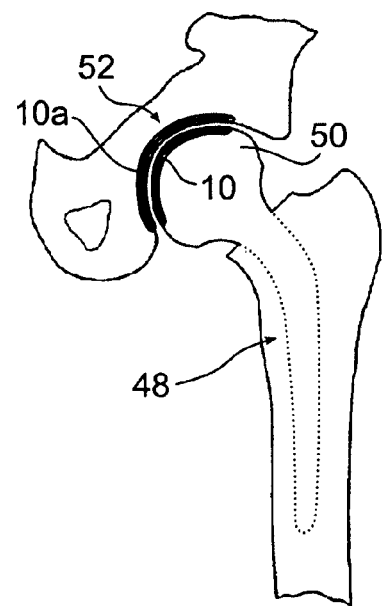
FIG. 5 is an illustration of magnetically active implants in accordance with the invention in association with a hip implant.

While the examples discussed above referred to the knee and spine, the embodiments of the invention may be applied in other contexts as well. For example, these concepts could be applied in a stem of an implant 48 so the head 50 is at least partially repelled from the acetabulum 52, as is shown in FIG. 5, just as the patella 54 could be at least partially repelled from the knee. It also could be used to distract joints temporarily to stretch out ligaments, to reduce pain from arthritis, or could be used to allow biologic resurfacing. For example, biologic resurfacing of a joint such as ACI, MACI, cartilage and/or bone grafting could be carried out and the invention may be used to distract the joint to allow improved range of motion. The implant elements could be placed across the joint on both sides of the joint to allow distraction of the joint and then could be selectively magnetized, turned on or off, or intermittently used.

The implant elements may also be placed in a collagen filter or collagen surface. The collagen could be placed in the bone or tissue to allow distraction of tissue. This may help decrease instances of adhesions. For example, in surgical applications the material could be selectively magnetized and demagnetized to help create an anti-adhesion barrier.

Insulators may also be placed on one or more sides of the implanted element so that the magnetic forces are applied only in a desired direction, or at least are screened from applying in an undesired direction.

Herein, magnetically active refers to magnets, electromagnets, or materials significantly attracted or repelled by same due to being magnetically permeable, and a magnetically active implant refers to an implant comprised of or containing a magnetically active material. Magnetic materials include neodymium (a combination of neodymium, iron, and boron), samarium-cobalt (SmCo5), ceramic, alnico (aluminum, nickel and cobalt), injection molded/bonded (formed from resins and magnetic powder), and plastic magnets, made from organic polymers. An example of an organic polymer is PANiCNQ, a combination of emeraldine-based polyaniline (PANi) and tetracyanoquinodimethane (TCNQ); however other biocompatible, as well as biodegradable polymeric polymers such as are known in the art and are to be developed may be advantageously used in accordance with the invention. Representative examples of magnetically permeable materials include, but are not limited to, mumetal (an alloy of nickel, iron, copper and molybdenum), permalloy (an allow of nickel and iron), iron, steel and soft ferrite.

Figure 6:
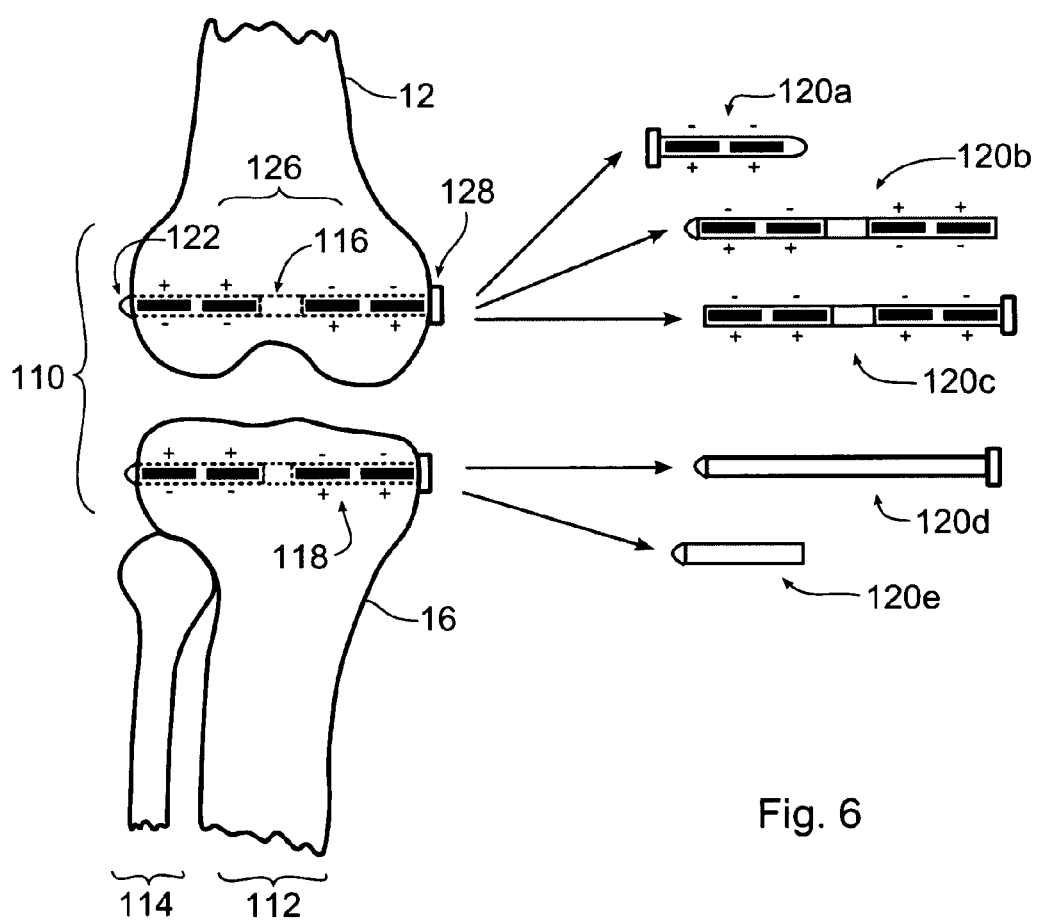
FIG. 6 illustrates alternative forms of magnetically active implants in accordance with the invention.

Various joint pathologies may be addressed by compressing or distracting the joint, or by compressing or distracting one side of a joint, medially or laterally, or by compressing one side of a joint while distracting the other side. It may further be beneficial to change these therapies during the course of healing. As can be seen in FIG. 6, magnetically active implants 116,118 are placed on opposing sides of a joint 100. In this embodiment, implants 116,188 are each magnetized, and similarly aligned so that like poles in each implant are disposed closest to each other.

As is well known in the art, when magnetic poles are aligned north (+) to south (−), two magnets will be attracted to each other, and conversely, when two magnets have the same pole aligned, they are repelled. Thus, in the embodiment shown in FIG. 6, a distractive force is applied to the joint. It should be understood that if two implants are intended to attract each other, at least one of the two must be magnetized or magnetizable material, and the other may merely be magnetically permeable, so that attraction may be achieved.

Implants 116,118 illustrate an elongated form, which may include a screw, rod, pin, cable, or bar. Implants in accordance with the embodiment shown in FIG. 6 may have a piercing tip 122 at a leading end, which may be self-drilling or tapping, or may otherwise operate to pierce cortical bone. Alternatively, the implants may have a leading end 124 that is blunt, as shown for implant 120c, wherein the implant would be inserted through an aperture formed in the cortical bone by known means. A shank 126 extends between the leading end and a head 128, which may contain means for driving or turning the implant, and or for anchoring the implant to cortical bone. Alternatively, the implant may not be provided with a head, as is shown in 120b, and the implant may be secured by other known means, such as bone cement.

To achieve compression of the joint, one of the implants 116,118 may be substituted with implant 120d, which comprises a magnetically permeable material. Alternatively, implant 118 may be inserted from the opposite side of bone 16, so that opposing poles of implants 116,188 are aligned. Alternatively, implant 116 may be formed with opposite polarity, whereby head 128 is proximate the south or negative pole. It should be understood that the alternatives thus described may be applied to either side of the joint to achieve compression, provided that the configuration results in opposite poles being juxtaposed, so that magnetic attraction occurs across the joint. Similarly, reorienting an implant, or inserting an implant with opposing polarity, may be applied to create distraction, provided that the configuration results in like poles being juxtaposed, so that magnetic repulsion occurs across the joint.

Implant 120a illustrates that an implant may be configured such that the implant passes through the cortical bone at only a single point. Implant 120a additionally illustrates that an implant may be sized to provide a greater impact on a portion of a joint, for example one side of joint. Accordingly, if two implants having a length as shown in 120a are disposed in association with one side of a joint, and have magnetic poles aligned properly, as described above, distraction or compression may be applied to a single side of a joint.

Additional implants 120a may be implanted, for example in both medial and lateral portions of bones on both sides of a joint, and so configured, in accordance with the methods described above, so that compression or distraction is applied to the entire joint. Alternatively, implants positioned on a medial side of a joint may exert a compressive force, while implants positioned on a lateral side of a joint exert a distractive force, and vice versa.

Implant 120a further illustrates that the implant may contain multiple magnetized or magnetizable elements, each representing a pair of magnetic poles indicated by "+" and "−" signs. These poles are alignable, for example as shown in implants 120a-c, so that the force is exerted along the length of the shank, and may be adjusted to control the force exerted across the joint. In the example shown in FIG. 120c, the poles are aligned so that a single implant may exert both a distractive and compressive force, in cooperation with a magnetically active implant on the opposite side of the joint.

It is convenient, in a further embodiment of the invention, for an implant including a magnetically active material to be formed in a variety of shaped forms, such as spheres, elliptical spheres, cones, cuboids, rods or combinations thereof, in a range of sizes. In this manner, the surgeon may select from a tray or kit containing an assortment of such implants, and may arrange implants of like or dissimilar sizes within the joint, in order to achieve the desired results, such as field strength and direction, while conforming to the anatomical space available.

Figure 7:
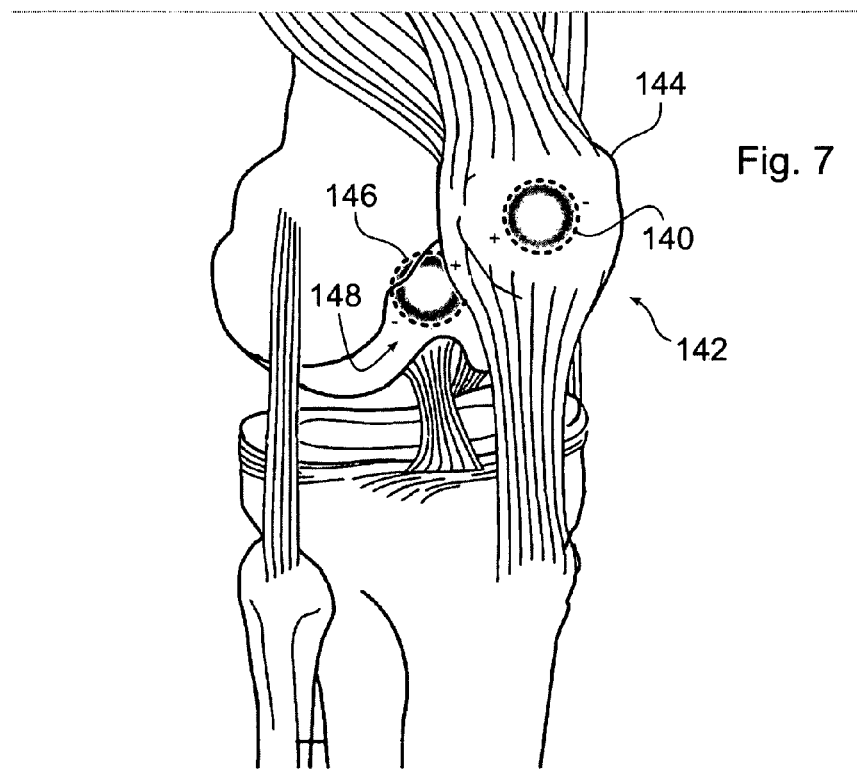
FIG. 7 illustrates a knee joint and patella with implants in accordance with the invention.

In an alternative embodiment in accordance with the invention, illustrated in FIG. 7, a magnetically active implant 140 is advantageously sized and shaped to fit the anatomy of the joint 142, to advantageously occupy a particular space available in the area of the joint, such as on the surface of a bone, either on the load bearing portion of the joint, or proximate the load bearing portion of the joint, or within the interior of the bone, or within a relief or channel formed in the bone, proximate the joint. Implant 140 is positioned at least partly within patella 144. An additional implant 146 is positioned at least partly within or near the trochlear groove 148. Implants 140,146 are depicted as being spherical, however, as described above, a variety of shapes and sizes are possible, as best suits the surgeon's purpose. As described with respect to FIG. 6, the implants are arranged so that the magnetic poles are operative to attract or repel as desired. The implants are then secured to the bone and or soft tissue using a suitable method, as is known in the art, or as otherwise described herein.

Further with respect to FIG. 7, Indeed, magnetically active implant having an arcuate shape, similar to the original trochlear groove, cooperative with a mating magnetically active implant associated with the patella, may operate to advantageously serve as a trochlear groove replacement, or may cooperate with the existing trochlear groove, to minimize forces operating on a diseased trochlear groove. This principle of mating shaped surfaces may be efficaciously applied to other joints in the body, in a like manner.

Figure 8:
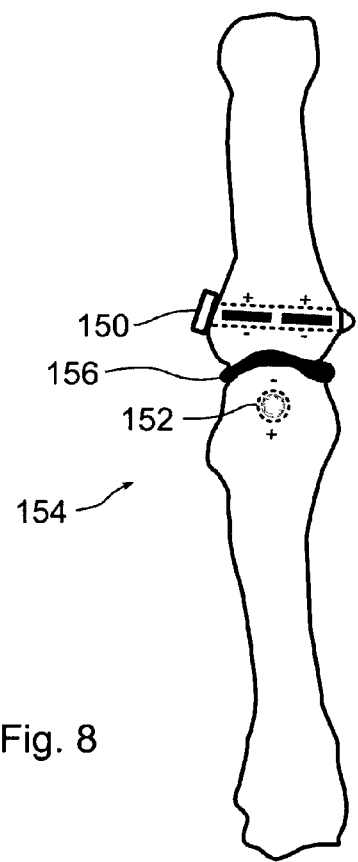
FIG. 8 is an illustration of implants and spacer in accordance with the invention, in association with a finger joint.

For example, FIG. 8 illustrates magnetically active implants 150,152 in the metacarpophalangeal (MCP) joint 154 of the hand. In one embodiment, a silicone spacer, 156, is implanted within the joint space, and can be compressed or distracted in association with implants 150,152, as indicated. Spacer 156 can act to decrease load on the joint, and can be used by the surgeon during arthroscopic procedures or during open reduction internal fixation (ORIF) to allow alignment of a joint or bone fragment. While the MCP joint is illustrated, the explanation applies equally to the carpometacarpal joint, or other joints, or bone on bone repairs within the body. Implant 150 further illustrates that magnetically active material may be fastened within the bone using a variety of means, such as are disclosed in U.S. Pat. Nos. 5,593,425 and 6,997,940 to Bonutti, which are incorporated herein by reference.

Figure 9:
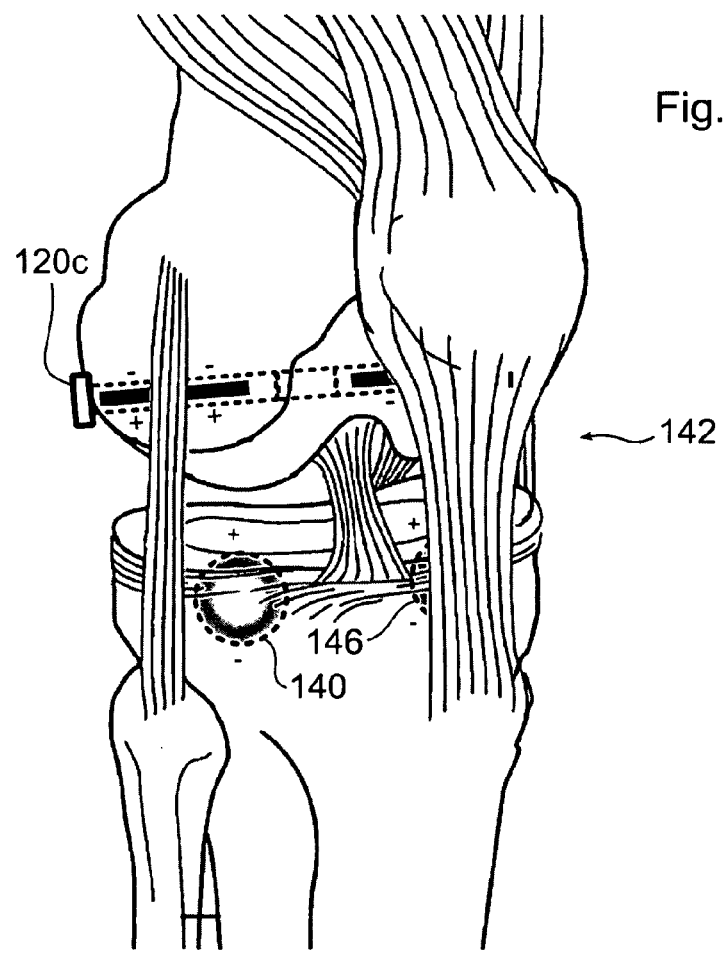
FIG. 9 is an illustration of magnetically active implants in accordance with the invention in association with the fibia and tibia.
Figure 10:
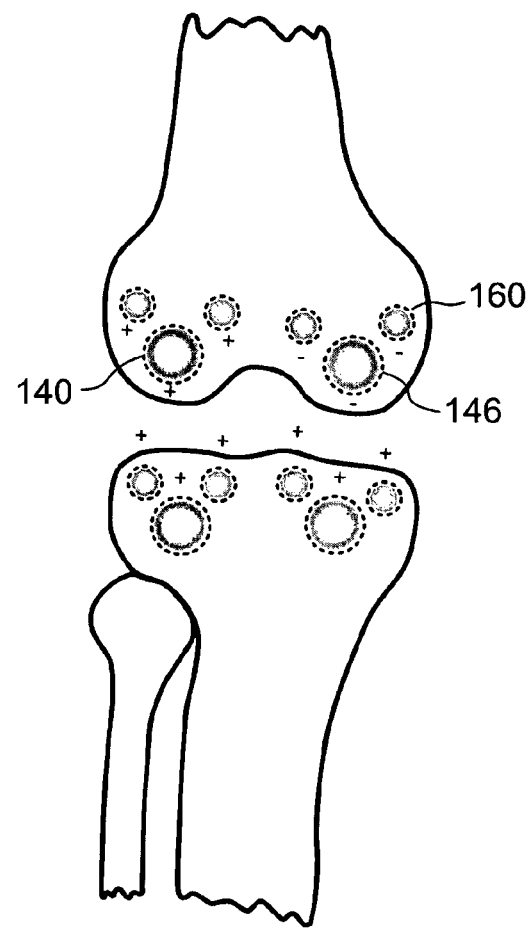
FIG. 10 is an illustration of various sized implants in accordance with the present invention, in a knee joint.

In FIG. 9, two different embodiments of magnetically active implants 120c and 140,146 in accordance with the invention cooperate to effectuate distraction of joint 142. FIG. 10 also illustrates two different embodiments of magnetically active implants in accordance with the invention, implant 140, and a reduced size form of implant 140, implant 160. In the particular configuration shown, a compressive force is exerted on the medial side of the joint, and a distractive force is exerted on the lateral side. Additionally illustrated is the ability to position implants of differing sizes 140,160, whereby space in the area of the joint is ideally utilized to position and orient the magnetic field, as well as to vary the strength of the magnetic field.

Figure 11:
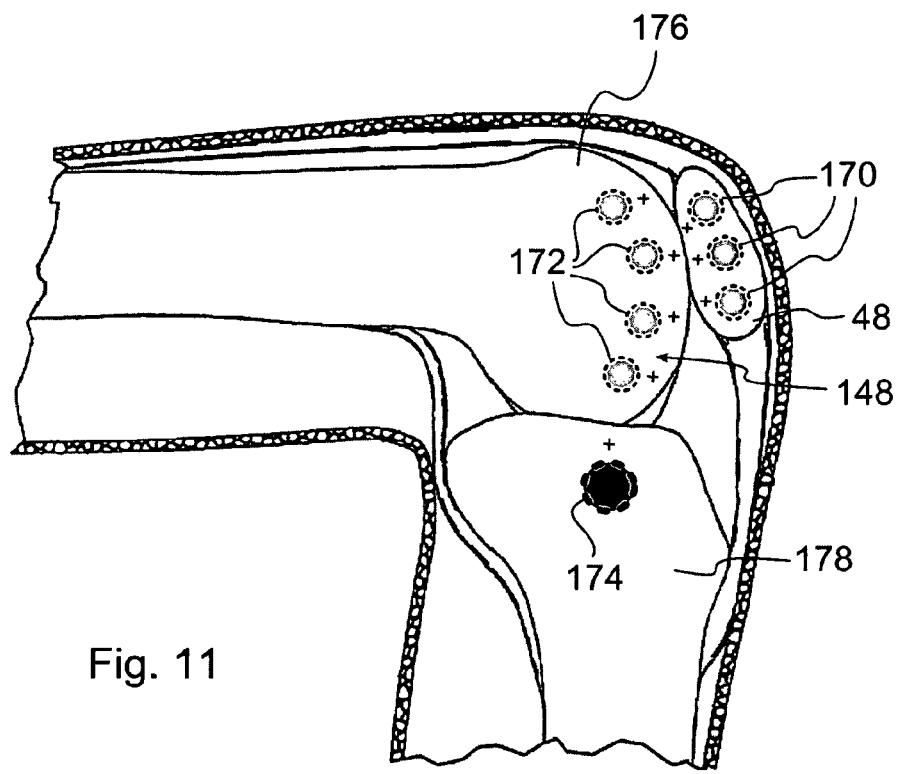
FIG. 11 is an illustration of another embodiment of the invention, in which implants cooperate through the range of motion of a joint.

With reference to FIG. 11, implants 170 are disposed within, partly within, on, or near the inner surface of the patella 48, and are positioned to cooperate with implants 172, disposed within, partly within, on, or near the distal end of the femur 176, or the trochlear groove 148, in particular. Accordingly, pressure at the patella trochlear interface may be reduced. In live tissue, this imparts the benefit of reduced wear on the joint, and may operate to alleviate pain associated with joint disease. Implants 170,172 may also be associated with joint replacement components associated with the femur, trochlea, patella, or any combination of same, to increase the longevity of the replacements. This is applicable to joints and joint replacement components used anywhere in the body, including the spine. Where it is desired to increase pressure in the joint, or bring joint components into closer conformity, polarity of the magnetic field may be revised to introduce attraction, and thus compression, instead of distraction.

In FIG. 11, implants 172 interact with implants 170 during a first portion of the range of motion of the joint, and implant 174, located within, partly within, on, or near the proximal end of tibia 178 during a second portion of the range of motion of the joint. In addition, during an intermediate portion of the range of motion, one or more of implants 172 may interact in part with one or more of implants 170, while one or more of implants 172 are interacting with implant 174. Further, implants 172 may be provided in other configurations for magnetically active implants such as are described elsewhere herein, including a singular, elongated implant formed as an arc, operative to interact with implants 170 and 174 in a like manner. Similarly, implants 170 may be provided in alternative shapes as herein described, including an integral magnetically active implant.

Figure 12:
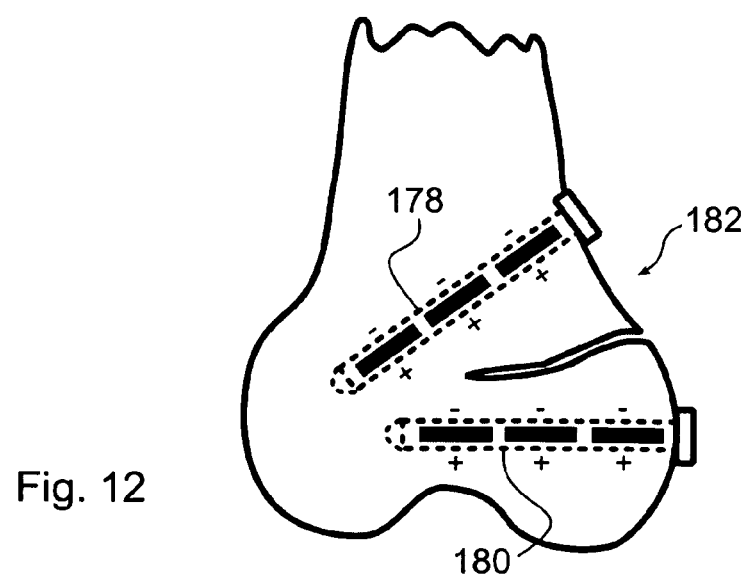
FIG. 12 illustrates implants in accordance with the invention applying a compressive force to a fracture.

With reference to FIG. 12, magnetically active implants 178,180 are placed adjacent to a fractured, separated or broken bone part 182, operative to provide a compressive force to promote healing. Implants 178,180 may advantageously take any of a variety of forms, such as are discussed herein, provided there is thereby established an attractive force operating across the affected area.

Figure 13:
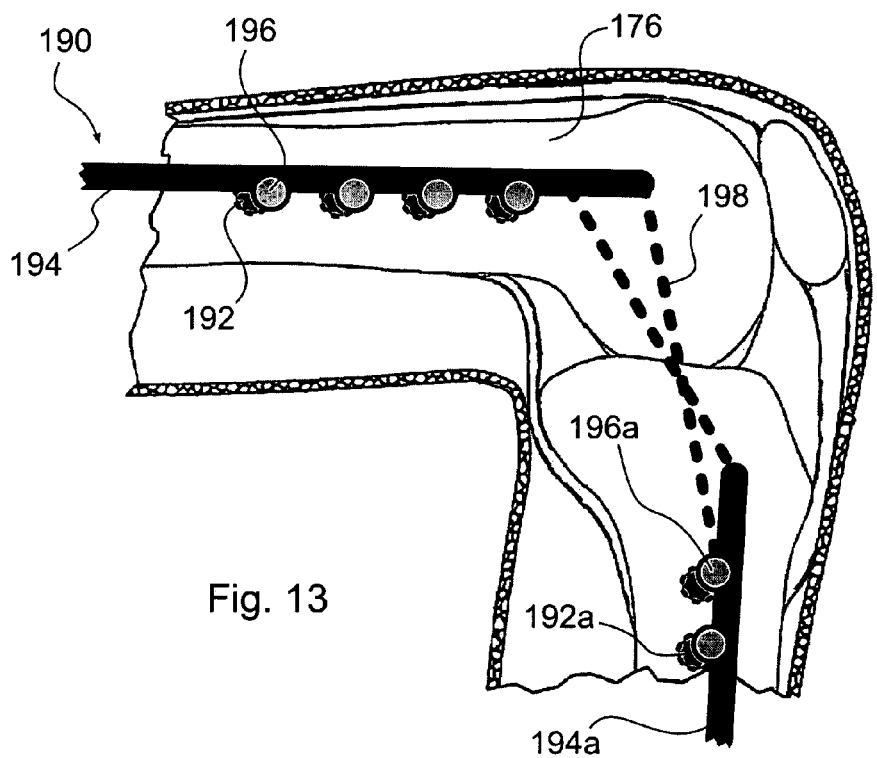
FIG. 13 is an illustration of a further embodiment of the invention, in which a brace is associated with magnetically active material that interacts with magnetically active implants.

Referring now to FIG. 13, movement of a joint, for example the knee joint 142, is influenced by an external device 190. In this embodiment, magnetically active material, indicated by implant 192 is implanted in engagement with at least one bone associated with a joint. An external device has a brace member, such as arm 194, contains magnetically active material, such as arm element 196, which is attracted to implant 192. A similar configuration may optionally be provided on the opposite side of the joint, as represented by implant 192a, arm 194a, and arm element 196a. As illustrated, implant 192,192a, as well as arm element 196,196a, may be provided as a series of magnetically active elements. Alternatively, implant 192,192a and arm element 196,196a may be provided in elongated form, or other shape, whereby a suitable magnetic attraction as is described herein is formed.

Due to the magnetic attraction between implant 192 and arm element 196, arm 194 becomes releasably connected to a bone on one side of a joint, herein represented by fibia 176. Through known means 198, arm 194 is connected to arm 194a, or alternatively to some other object, such as a structure for physical therapy, apparatus for locomotion, or other fixture or appurtenance (not shown). In this manner, means 198 may provide a resistive force, an assistive force, or a combination of the two, though mechanical; hydraulic; electromechanical, possibly including computer control; or other known means. As such, a brace operative to provide a therapeutic or locomotive benefit may be releasably connected or affixed to a body. More particularly, straps, adhesives, clamps, rods, or other means of connecting devices to the body may be avoided. This eliminates or reduces the discomfort, pressure, abrasion, compression, inflammation, and related maladies and injuries associated with attachment of a physical device to the body, and in particular to the skin. Of course, this is particularly beneficial for avoiding fixation involving skin penetrations.

Figure 14:
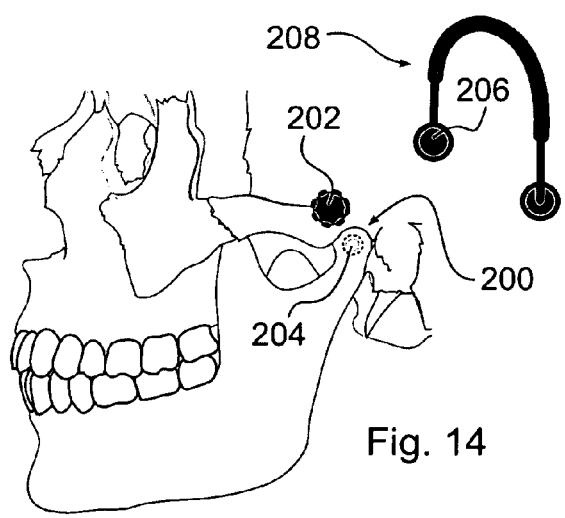
FIG. 14 illustrates magnetically active implants and external magnetically active means in accordance with the invention, operative to provide therapeutic benefit to a jaw.

With reference to FIG. 14, magnetically active implants in accordance with the current invention can be used to address temporomandibular joint disorder, by influencing the alignment of the temporomandibular joint 200. Magnetically active implant 202 is disposed proximate the joint, in attachment to the skull, aligned with magnetically active implant 204, so that the direction of magnetic force is appropriate to the pathology to be addressed. Polarity of the magnets may be arranged to either distract or compress the joint, or to reposition the mandible to achieve a desired therapeutic result. Implant 204 may alternatively be attracted or repelled by a magnetically active element 206 located outside the body, and aligned with implant 204 through attachment to known securing means, such as head gear 208, shown in part.

Figure 15:
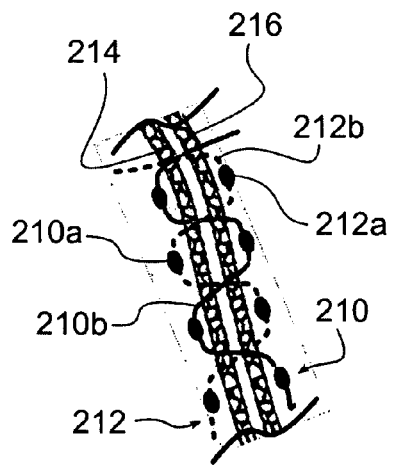
FIG. 15 is an illustration of magnetically active sutures in accordance with the invention.

In another embodiment of the invention, shown in FIG. 15, magnetically active suture elements 210,212 retain separated body tissue members 214,216 in healable proximity. In the illustration, magnetically active portions 210a,212a are illustrated in possibly exaggerated form, for clarity. Either suture 210,212 is introduced into body tissue using known means. Suture segments 210b,212b are illustrated with different shading so that they may be differentiated; however, it should be understood that portions may appear above or below the tissue, or within the tissue, according to the suturing method employed. In the embodiment shown, a stitching pattern is employed whereby portions 210a are magnetized, and are disposed opposite portions 212a, which are magnetically permeable. Alternatively, either suture element 210,212 may be used independently, turning back on itself, or forming loops, so that appropriately polarized, or attracting segments of the suture are disposed in correct proximity, one to the other. In addition to forming the suture with discrete magnetic portions 210a,212a, the entire suture could be magnetized, particularly where formed using a magnetic polymer, or other flexible magnetic material. An additional advantage is the potential for fewer skin penetrations during stitching, or the elimination of visible stitches entirely, through the use of subcutaneous stitching, and a final closure through the use of magnetically active elements adhered or otherwise affixed to the final layer of skin, disposed on opposite sides of the incision, or beneath and above the skin, operative to hold the final layer of skin closed until healed. The implanted magnetically active element could thus be advantageously formed with a biodegradable magnetic polymer.

During use, tissue is maintained in proximity through the combined force of the stitching, as well as either the magnetic attraction between portions 210a,212a, or the interaction between magnetically active suture lengths, as described. In all embodiments, there is a particular advantageous where the tissues are soft or otherwise easily torn by known sutures.

Figure 16:
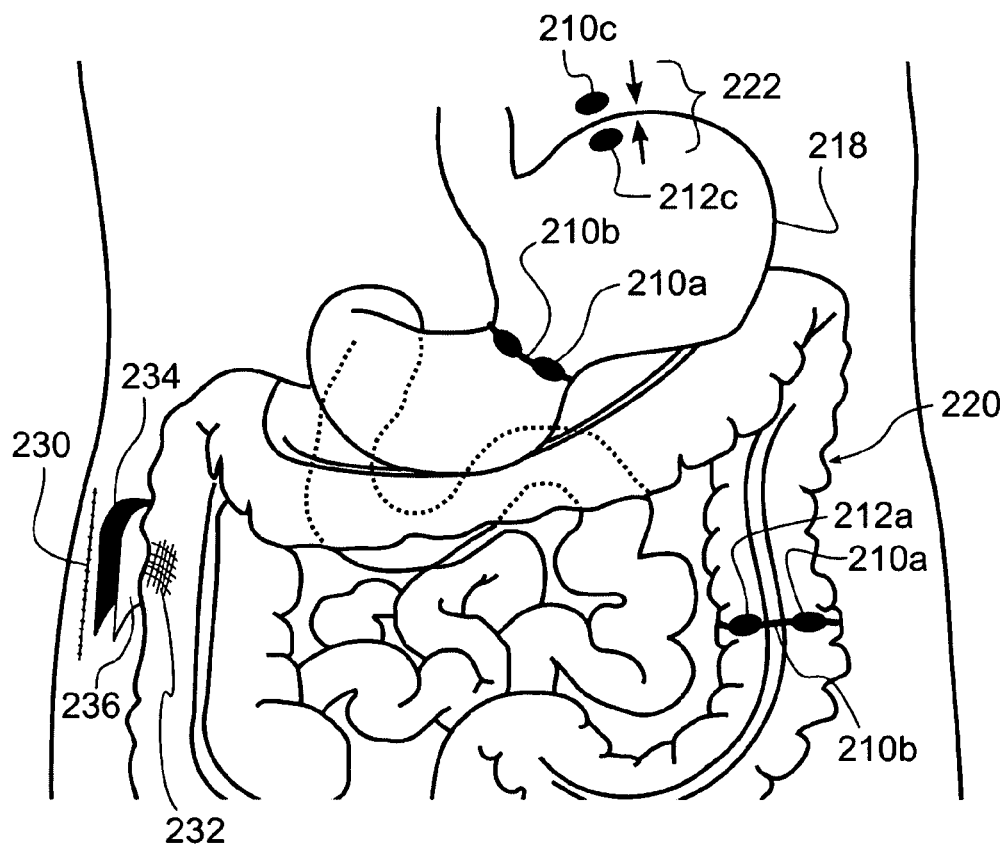
FIG. 16 illustrates magnetically active elements in accordance with the invention, operative to change the shape and position of soft tissue.

Implants in accordance with the invention may also be used to reshape soft tissue, including increasing, maintaining, or decreasing the amount of space defined by the soft tissue. With reference to FIG. 16, implants are fastened to soft tissue, such as stomach 218, or large intestine 220. The implants may take the form of magnetically active suture element 210, or other suture elements as discussed above, and be sutured into connection with soft tissue, or they may be attached, fastened or affixed by other means, including mechanical means, such as bands, adhesives, sutures, staples, and clips, or by magnetic attraction, as by pinching soft tissue (arrows 222) between two magnetically active members 210c,212c. In the latter configuration, member 210c may be removed, and member 212c may then remain in attachment to soft tissue, for future therapeutic treatment, or be removed through digestion or intervention.

Magnetically active implants in accordance with the invention, in connection with soft tissue, may be attracted or repelled to each other in order modifying the location or the shape of the space defined by the soft tissue to which they are attached. Magnetically active implants attached to soft tissue may be arranged to attract and or repel each other in order to increase or decrease the volumetric space, to block or allow the passage of fluids or other materials within a vessel or chamber, or to maintain separate soft tissue together, or apart. As illustrated in FIG. 16, stomach 218 is constricted using means described above. In a like manner, a reduction in space can be used for hemostasis, and for decreasing space and reducing the formation of seromas, hematomas, abscesses, fistulas, olecranon bursa swelling, and the like. In a similar manner, intestine 220 is maintained in an open configuration through magnetically active elements 212a and 210a, which are instead arranged in connection with soft tissue to be repelled, and thus to form an open circle, or arc, or other therapeutically beneficial shape.

Soft tissue which has been abraded, cut, or damaged 230,232, as by surgery or trauma, may form adhesions, or scar tissue within the body. These tissue formations can cause pain, and may require surgery in order to be removed. Failure to remove them can lead to illness, and in some cases death. In accordance with the invention, healing tissue may be separated from other tissue through the use of magnetically active implants. In this manner, tissues may be maintained in non-contacting conformity while healing, thereby reducing the incidence and severity of the formation of adhesions. Magnetically active implants may be used to bind or otherwise physically maintain tissue layers apart, such as is described with respect to implants 210a,212a of FIG. 16. Alternatively flat magnetically charged polymer sheets or shaped members 230,232 may be interposed between healing regions, and magnetically repelled one from the other, thereby forming a gap between healing tissues. Shaped members 234,236 may be fixed into place by any of the methods described herein for fastening magnetically active implants in accordance with the invention.

It is further contemplated that one or more magnetically active elements are located outside the body, operative to attract a magnetically active implant associated with soft tissue, and thus influence the location, shape or position of soft tissue within the body.

In yet another embodiment in accordance with the invention, soft tissue is positioned or shaped with respect to bone, or is connected to bone, using at least one magnetically active implant in accordance with the invention, as described herein.

Figure 17:
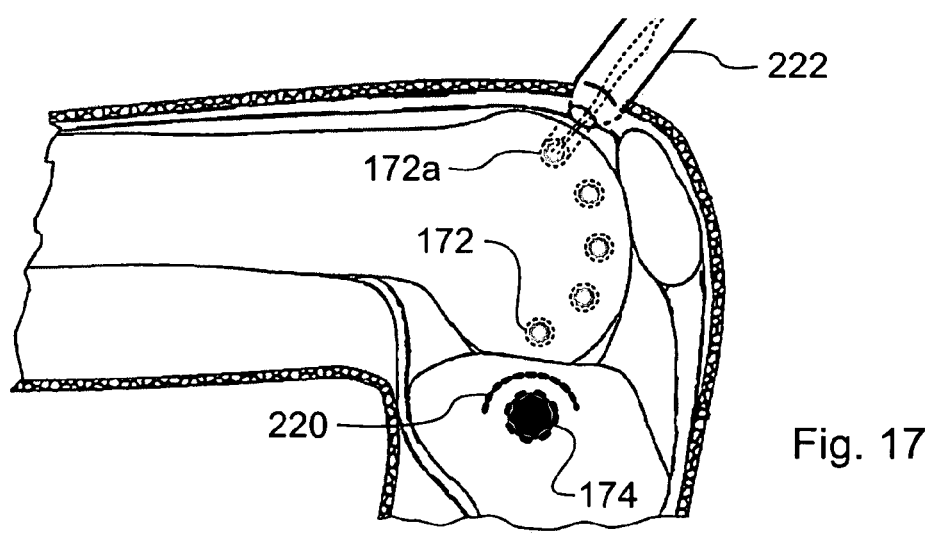
FIG. 17 is an illustration of implantation using a cannula, as well as magnetic shielding, in accordance with the invention.

In another embodiment of the invention, magnetic shielding is provided to control the force of magnetic fields between magnetically active implants. With reference to FIG. 17, shield 220 is positioned operative to reduce the magnetic attraction between implants 172 and 174. Shielding is accomplished using known methods, such as placing a magnetically permeable material between a magnetically active implant and another magnetically active implant, or between a magnetically active implant and a magnetically active material which is not intended to be influenced by the magnetically active implant, or to reduce a magnetic field extending outside the body. The shielding may be selectively positioned to be interposed between two or more magnetically active members where it is intended to disrupt the magnetic field, and removed or repositioned when it is desired to restore the magnetic field.

Cannula 222, illustrated in FIG. 17, may be used to insert a magnetically active implant in accordance with the invention, such as implant 172a. Using minimally invasive surgical procedures, a small incision is formed in the skin proximate the situs of implantation. Using methods further described in U.S. Pat. Nos. 6,814,715 and 7,104,996, to the instant inventor, incorporated herein by reference, implantation is achieved with a minimum of trauma and disruption to the body.

The implants may be provided with a porous surface, or may have apertures, to promote bone ingrowth. The implants may further be coated with a material which promotes bone growth and or ingrowth. This provides benefits including better integration, stabilization, and healing of the implant within the implant environment. It is further contemplated that a delivery system may be used with the present invention. For example, the implants may be coated with a biostable or biodegradeable material which releases therapeutic agents at the site of the implant, including antibiotics, hydroxypatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, bone growth inducing material, osteoinductive materials, apatite compositions with collagen, or demineralized bone powder. U.S. Patent Publication 2007-0141106 A1, to the instant inventor, entitled "Drug Eluting Implant", discloses means for delivering therapeutic agents, and is incorporated herein by reference in its entirety.

Implants in accordance with the invention may be substantially smaller than are illustrated herein. The size of the implant may be dictated by the type and strength of magnetic energy required. Microscopic and nanoscopic implants are additionally contemplated, as well as nanoengineered magnetically active implants.

A device in accordance with the invention may be used to compress a lateral side of a joint, and to distract a medial side of a joint, or vice versa, much like an unloader brace.

Figure 18:
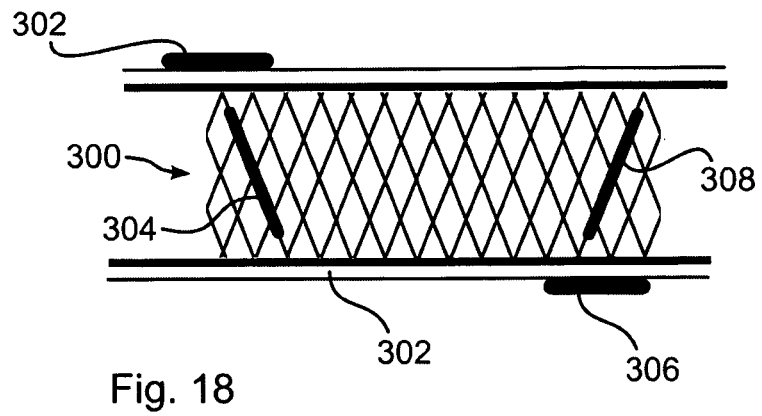
FIG. 18 illustrates a stent within the body containing magnetically active materials, cooperative with implants in accordance with the invention for improved blood flow, or for precise positioning of the stent.

With reference to FIG. 18, implants 304,306,308,310 in accordance with the invention may also be placed in a stent 300 and or along a lumen 302 wall, to aid in positioning or maintaining a position of stent 300 within the body, as in a particular position within lumen 302. Implants 304,306,308, 310 may be either magnetized or magnetically active. In one embodiment, implants 302 and 304 are attracted, and implants 306 and 308 are attracted, but not implants 302 and 308, or implants 306 and 304. In this manner, precise positioning may be more easily accomplished and maintained. Such implants may additionally be used to improve blood flow through the stent implant area, including creating a better laminar flow, or an optimized laminar flow.

Figure 19:
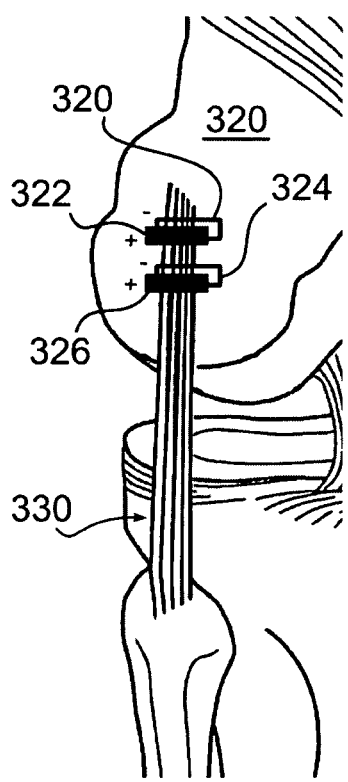
FIG. 19 illustrates implants in accordance with the invention operative to maintain ligamentous or other body tissue in a proper location.

Referring to FIG. 19, implant elements 320,322,324,326 may also be used for ligament 330 repair or biologic resurfacing, to affix ligament 330 or surface in place, or to relieve pressure on the tissue during healing. Such support is additionally useful for pain management. In FIG. 19, elements 320,324 are affixed relative to bone 332, and elements 322,326, optionally affixed to ligament 330, are magnetically attracted to elements 320,324.

Figure 20:
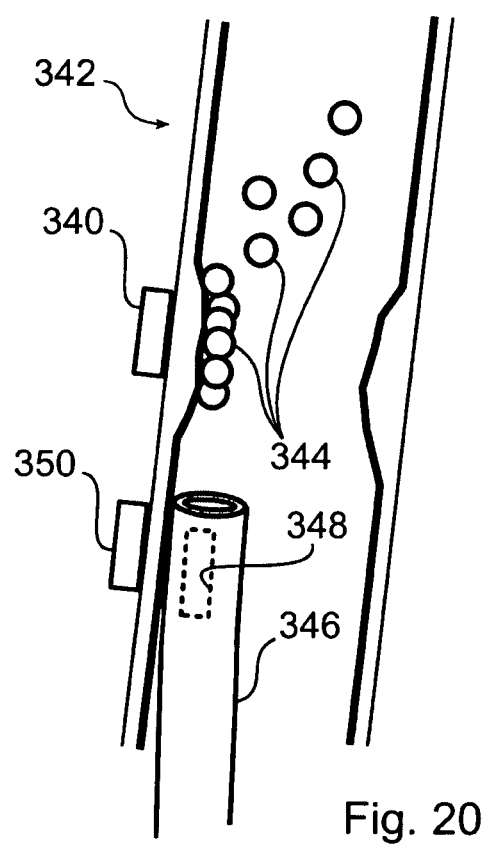
FIG. 20 illustrates implants in accordance with the invention operative to attract magnetically active particles to a treatment site within the body, and operative to precisely position a tool within the body.

In a further embodiment in accordance with the invention, and with reference to FIG. 20, implants 340 in accordance with the invention may be used for oncologic surgery, spine surgery, or cranial surgery, the surgical environment of each represented figuratively by 342. Methods include positioning therapeutic agents 344 within an area to be treated, the therapeutic agents containing a magnetically active material. Additionally, an instrument 346, such as for example a catheter, may be positioned or maintained in position with precision and further control through attraction between a magnetically active material 348 connected to instrument 346, and an implant 350 in accordance with the invention.

Figure 21:
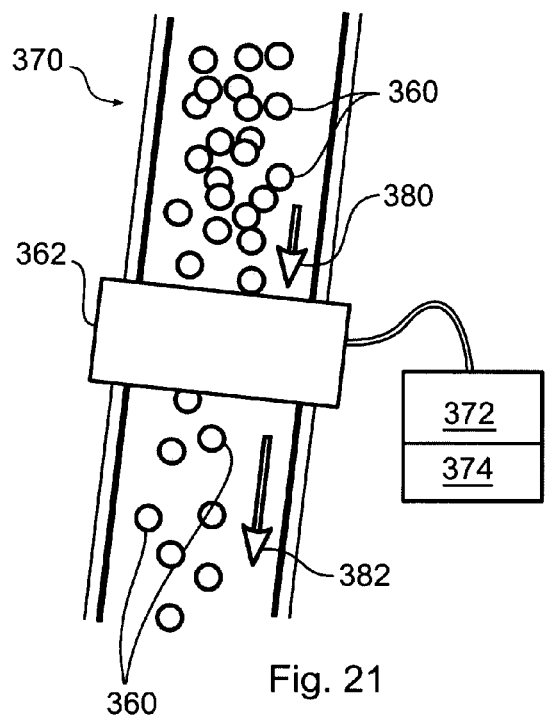
FIG. 21 is an illustration of a space within the body at least partially surrounded by an implant in accordance with the invention, the implant energized by a controller connected to an energy source, the implant operative to improve flow of magnetically active material through the space.

In accordance with the invention, and with reference to FIG. 21, iron particles in hemoglobin within blood cells 360 are magnetically attracted and repelled by implant 362 in accordance with the invention, and blood flow in the body is improved. Implants 362 is provided to at least partially surround blood vessel 370, and has a magnetic polarity switchable by mechanical or electronic controller 372, connected to a source of energy 374. Implant 362 thus attracts blood cells and repels them downstream, increasing velocity, and overall flow volume, as indicated by short upstream arrow 380 and longer downstream arrow 382. Magnetic activity of blood cells is improvable by electrically charging blood cells upstream of the location of implant 362. In this manner, more oxygen and or more nutrients may be delivered to a specific site, speeding healing and growth. Similarly, other charged or magnetically active particles may be introduced into the bloodstream, and concentrated in an intended region by improved flow as described, to either alter the microclimate, for example by introducing pH changing agents, or to deliver nutrients or therapeutic substances. A similar accelerating/concentrating functionality may be imparted to a stent, such as stent 300 shown in FIG. 18.

Figure 22:
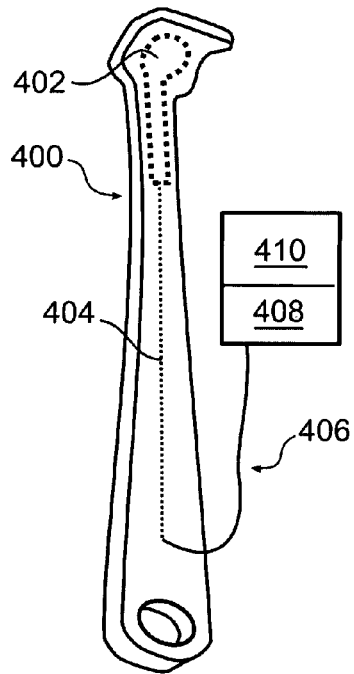
FIG. 22 illustrates a surgical tool in accordance with the invention containing a magnetically active material, and a controller operative to energize the material.

With reference to FIG. 22, in another embodiment of the invention, tools such as clamps or retractors, such as retractor 400, contain magnetically active material 402, and cooperate with implants in accordance with the invention to attain or maintain a position, to improve the grip or performance of a tool, to keep tissue out of the way, or to enhance exposure, or could be used with computer assisted navigation as an adjunct to guidance. Material 402 may have the form of magnetized material, or may be an electromagnet, as shown. Wire 404 within the tool is connected at 406 to a power source 408, and optionally to a computer 410, wherein the computer senses when the tool is proximate an implant in accordance with the invention through a change in the electrical signal in wire 406 induced by a change in the magnetic field between the implant and magnetically active material 402.

Figure 23:
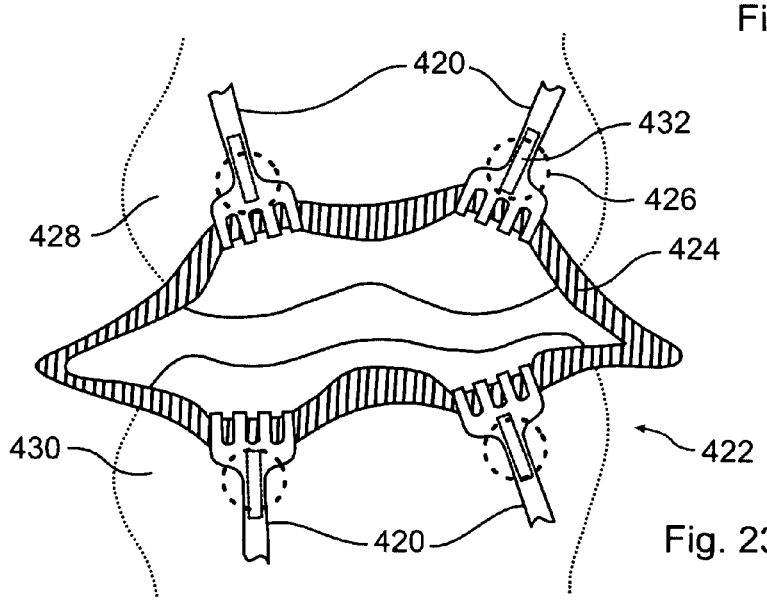
FIG. 23 illustrates a surgical field, wherein tools in accordance with the invention are located and or attracted to a position in relation to the body in cooperation with implants in accordance with the invention.

Referring now to FIG. 23, tools 420 as described with respect to FIG. 22 is employed within surgical field 422, in this embodiment retracting tissue 424. Implants 426 in accordance with the invention are positioned with respect to a landmark on or in the body, in this embodiment positions on bones 428 and 430. Magnetically active material 432, attached to or within tool 420, may have the form of a permanent magnet, or an electromagnet, as illustrated in FIG. 22. Magnetically active material 432 may operate to secure tool 420 with respect to implant 426, and/or to assist in navigation, as described with respect to FIG. 22. While retractors and a joint space are illustrated in FIG. 23, it should be understood that tool 420 could be any surgical tool or instrument that would not be adversely affected by a magnetic field, and such tools can be used in many different types of surgical procedures.

Referring again to FIG. 13, it should be understood that, in addition to braces, other wearable items, such as shoes or other orthotics, may be provided with magnetically active elements cooperative with implants in accordance with the invention. Such configurations can be employed for arthrodiastasis, as well as improving range of motion.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. An apparatus for first and second bones of a joint in a body, the apparatus comprising:
    at least one electromagnet configured to be implanted in the body or in the first bone of the joint and generate a magnetic field from in the body;
    a control unit electrically coupled to said at least one electromagnet and configured to energize said at least one electromagnet;
    a sensor electrically coupled to the control unit; and
    an implant configured to be implanted in the body on or in the second bone of the joint and at least attracted to or repelled by said electromagnet, wherein the implant has a surface configured to promote tissue ingrowth,
    wherein said control unit includes at least one of an analog to digital converter, a drive circuit, and a manually operated control,
    wherein said control unit is configured to automatically adjust separation or proximity of the first and second bones of the joint by dynamically controlling at least one of an intensity and a polarity of said at least one electromagnet from a first activated setting to a second activated setting, based on a signal received from said sensor,
    wherein the dynamic control of at least one of the intensity and the polarity of the at least one electromagnet assists movement of the joint from at least one first position to at least one second position, and
    wherein the signal received from the sensor dynamically controls at least one of the intensity and the polarity of the at least one electromagnet from the first activated setting to the second activated setting in order to improve the power management of the at least one electromagnet.

2. The apparatus of claim 1, wherein said sensor is configured to monitor a parameter of the body, the parameter including at least one of a resting state, orientation, temperature, compression, blood pressure, pulse rate, fluid viscosity, oxygen level, acid level, and personal control.

3. The apparatus of claim 1, wherein said sensor is configured to monitor a parameter of the joint, the parameter including at least one of a pressure, angular displacement, rotational displacement, orientation, movement, temperature, fluid viscosity, oxygen level, and pH level.

4. The apparatus of claim 1, wherein the joint is at least one of a finger, wrist, elbow, shoulder, spine, hip, knee, ankle and toe.

5. The apparatus of claim 1, wherein said implant is an electromagnet energizable by said control unit.

6. The apparatus of claim 1, wherein said sensor is configured to be positionable externally or internally with respect to the body.

7. The apparatus of claim 1, wherein said sensor is configured to respond to a change in voltage due to a change in proximity of said electromagnet and said implant.

8. The apparatus of claim 1, wherein a magnetic field generated by the at least one electromagnet is dynamically adjustable based on pressure exerted on the first bone of the joint.

9. The apparatus of claim 8, wherein the magnetic field is dynamically adjusted by varying voltage or duty cycle of voltage applied to the at least one electromagnet.

10. The apparatus of claim 9, wherein the applied voltage decreases with a decrease in pressure exerted on the first bone of the joint.

11. The apparatus of claim 1, wherein the joint includes collagen, wherein said control unit is configured to automatically adjust separation or proximity of the first bone and collagen of the joint by adjusting at least one of an intensity and a polarity of said at least one electromagnet.

12. An apparatus for first and second bones of a joint in a body, the apparatus comprising:
    an electromagnet configured to be implanted in the body or in the first bone of the joint and generate a magnetic field in the body;
    a control unit electrically coupled to said electromagnet and configured to energize said electromagnet;
    an implant element configured to be implanted in the body on or in the second bone of the joint and at least attracted to or repelled by said electromagnet to adjust separation or proximity of the first and second bones of the joint, wherein the implant element has a surface configured to promote tissue ingrowth; and
    a force detecting device electrically coupled to said control unit, said force detecting device configured to measure at least one physiological parameter of the joint,
    wherein said control unit includes at least one of an analog to digital converter, a drive circuit, and a manually operated control,
    wherein said force detecting device provides an output to said control unit to dynamically control at least one of an intensity and a polarity of said electromagnet from a first activated setting to a second activated setting to adjust separation or proximity of the first and second bones of the joint, based on a change in loading or position of the joint,
    wherein the dynamic control of at least one of the intensity and the polarity of the electromagnet assists movement of the joint from at least one first position to at least one second position, and
    wherein the signal received from the force detecting device dynamically controls at least one of the intensity and the polarity of the electromagnet from the first activated setting to the second activated setting in order to improve the power management of the electromagnet.

13. The apparatus of claim 12, wherein the joint includes collagen, wherein said control unit is configured to adjust separation or proximity of the first bone and collagen of the joint based on an output received from said force detecting device to adjust at least one of an intensity and a polarity of said electromagnet.

14. An apparatus for first and second bones of a joint in a body, the apparatus comprising:
    a first electromagnet configured to be implanted in the body or in the first bone of the joint and generate a first magnetic field from in the body;
    a second electromagnet configured to be implanted in the body on or in the second bone of the joint and generate a second magnetic field from the body;
    a control unit electrically coupled to said first and second electromagnets and configured to energize said first and second electromagnets; and
    a sensor electrically coupled to said control unit, wherein said control unit includes at least one of an analog to digital converter, a drive circuit, and a manually operated control, wherein said control unit is configured to change the first or second magnetic field to dynamically control at least one of an intensity and a polarity of at least one of said first and second electromagnets from a first activated setting to a second activated setting to adjust separation or proximity of the first and second bones of the joint, based on a measured change in loading or position of the joint, wherein the dynamic control of at least one of the intensity and the polarity of at least one of the first and second electromagnets assists movement of the joint from at least one first position to at least one second position, based on a measured change in loading or position of the joint, wherein the signal received from the force detecting device dynamically controls at least one of the intensity and the polarity of at least one of the first and second electromagnets from the first activated setting to the second activated setting in order to improve the power management of at least one of the first and second electromagnet, based on a measured change in loading or position of the joint, and wherein at least one of the first electromagnet and the second electromagnet has a surface configured to promote tissue ingrowth.

15. The apparatus of claim 14, wherein at least the first or second bone includes collagen.

16. The apparatus of claim 14, wherein at least the first or second bone includes an implant.

* * * * *